United States Patent
Perego et al.

(10) Patent No.: US 7,115,537 B2
(45) Date of Patent: Oct. 3, 2006

(54) PROCESS FOR THE REGENERATION OF ZEOLITE CATALYSTS

(75) Inventors: Carlo Perego, Carnate (IT); Alberto De Angelis, Legnano (IT); Otello Faris, Rome (IT); Aldo Bosetti, Vercelli (IT)

(73) Assignee: Dow Global Technologies Inc., Midland, MI (US)

( * ) Notice: Subject to any disclaimer, the term of this patent is extended or adjusted under 35 U.S.C. 154(b) by 146 days.

(21) Appl. No.: 10/312,160

(22) PCT Filed: Jun. 22, 2001

(86) PCT No.: PCT/EP01/07113

§ 371 (c)(1),
(2), (4) Date: Sep. 4, 2003

(87) PCT Pub. No.: WO01/97969

PCT Pub. Date: Dec. 27, 2001

(65) Prior Publication Data

US 2004/0092772 A1      May 13, 2004

(30) Foreign Application Priority Data

Jun. 22, 2000   (IT) ........................... MI2000A1404

(51) Int. Cl.
*B01J 20/34*    (2006.01)

(52) U.S. Cl. ............. 502/22; 502/26; 502/27; 502/28; 502/29; 502/30; 502/31; 502/32; 502/33

(58) Field of Classification Search ............. 502/60, 502/63, 64, 67, 71
See application file for complete search history.

(56) References Cited

U.S. PATENT DOCUMENTS 4,908,341 A * 3/1990 Pruden et al. ............. 502/30
5,241,119 A * 8/1993 Clerici et al. ............. 564/332

OTHER PUBLICATIONS

Organic Chemistry 4th edition, Pine et al., McGraw-Hill Book Co., NY, 1980, p. 615.*

* cited by examiner

*Primary Examiner*—Brian Davis

(57) ABSTRACT

A process for the regeneration of a zeolitic catalyst which is at least partially exhausted by use in the synthesis of optionally substituted methylenedianiline (MDA) and derivatives thereof, or of a mixture of optionally substituted MDA and derivatives thereof, with a higher homologous product the process involving washing said catalyst with an aromatic compound having at least one substitutent on the aromatic ring having activating characteristics with respect to the electrophilic substitution, in liquid or at least partially liquid phase.

11 Claims, No Drawings

PROCESS FOR THE REGENERATION OF ZEOLITE CATALYSTS

The present invention relates to a process for the regeneration of a zeolitic catalyst. More specifically, the present invention relates to a process for the regeneration of a zeolitic catalyst used in the preparation of optionally substituted methylenedianiline (MDA) and derivatives thereof, or of mixtures of optionally substituted MDA and derivatives thereof, and a higher homologous product. Suitably, optionally substituted MDA and derivatives thereof and mixtures of optionally substituted MDA and derivatives thereof together with a higher homologous product contain a compound of formula (I):

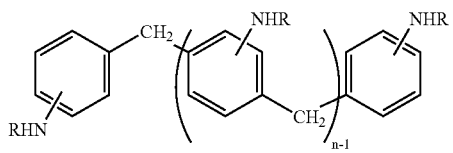

wherein R represents independently hydrogen, a $C_1$–$C_8$ alkyl, $C_4$–$C_{10}$ cycloalkyl $C_6$–$C_{12}$ aromatic radical and n is an integer greater than or equal to one, such as to give a functionality ranging from 2 to 6. n is suitably from 1 to 5.

The term "derivatives thereof" when used in relation to MDI denotes compounds in which one or more of the amine groups attached to the aromatic rings is a secondary amine, that is where R is not hydrogen.

The term higher "homologous product" denotes a compound of formula I where n is at least 2 and thus comprises a compound having at least 3 aromatic rings each with an amine group and being optionally substituted and being linked by methylene groups.

Optionally substituted methylenedianiline and derivatives thereof or mixtures of optionally substituted methylenedianiline and derivatives thereof, with a higher homologous product, may be used as intermediates in the preparation of isocyanates in which at least one of the amine groups is converted into an isocyanate group, hereinafter referred to as a "corresponding isocyanate". The corresponding isocyanates may be used in the synthesis of different types of compounds including for example polyurethanes, thermoplastic polymers and epoxy resins.

Methylenedianiline may be produced from aniline or one of its derivatives by condensation with formaldehyde in the presence of a strong acid solution, for example hydrochloric acid, sulfuric acid and phosphoric acid, as described, for example, in U.S. Pat. Nos. 2,683,730, 3,277,173, 3,344,162, 3,362,979 or in H. Ulrich, "Chemistry and Technology of Isocyanates" John Wiley and Sons, USA, 1996. The operating conditions necessary for producing a product with certain structural characteristics and without the formation of significant quantities of by-products, may require the use of a large quantity of a strong acid. Under these circumstances, materials capable of resisting these acids are suitably used in the plant. Such materials are often expensive. Furthermore, once MDA has been synthesized, a corresponding quantity of base (typically sodium carbonate) is typically used to neutralize the acid used, causing the formation of large quantities of salts which must be disposed of. All these requirements lead to an increase in the production costs and difficulties in running the process.

In order to address the above drawbacks, improvements in processes for producing MDI have been proposed, which have led to the use of solid acid catalysts in substitution of the traditional inorganic acids. U.S. Pat. Nos. 4,039,580, 4,039,581, 4,092,343 and 4,294,987, for example, describe the use of clays and diatomaceous earth as catalysts in the synthesis of MDA. U.S. Pat. No. 5,241,119 describes a process for the preparation of 4,4'-diamino-diphenyl methane which comprises the reaction between aniline and formaldehyde in the presence of a solid catalyst selected from zeolites, in particular Y zeolite, ZSM-5 zeolite, zeolites modified with one or more of the following metals: aluminum, boron, iron and titanium. The reaction is carried out in a solvent at a temperature ranging from 50 to 200° C., at a pressure depending on the boiling point of the solvent used.

Italian patent applications M199A-1171 and M199A-1988 M12000A681 describe synthesis processes of MDA and its higher homologous products, respectively using, as solid acid catalysts, zeolites with a "spaciousness index" ranging from 2.5 to 19, for example beta zeolite, or silico-aluminas amorphous to X-rays, with a molar ratio $SiO_2$/$Al_2O_3$ from 10/1 to 500/1 and having a surface area from 500 to 1000 m$^2$/g, a porosity from 0.3 to 0.6 ml/g and a pore diameter from 20 to 500 Å.

Solid catalysts, however, may also have disadvantages as they may lose their activity with use due to the formation of pitches and/or carbonaceous residues. It is believed that the residues are deposited on the solid catalyst, block the pores in the solid and therefore reduce its contact surface. For this reason, solid acid catalysts are typically regenerated at a high temperature, even higher than 500° C., and in the presence of an oxidizing gas, air or oxygen, with a consequent increase in the production costs.

The Applicants have now found a process for the regeneration of a zeolitic catalyst which is at least partially exhausted by use in the synthesis of optionally substituted methylenedianiline (MDA) and derivatives thereof or of mixtures of optionally substituted MDA and derivatives thereof with a higher homologous product starting from the re-arrangement reaction of the corresponding aminal intermediate or the direct condensation reaction between formaldehyde and optionally substituted aniline or a derivative thereof, the process comprising subjecting said catalyst to a treatment of the chemical type thus avoiding, postponing or reducing the need for high temperature thermal treatment.

The object of the present invention therefore relates to a process for the regeneration of a zeolitic catalyst which is at least partially exhausted by use in the synthesis of optionally substituted methylenedianiline (MDA) and derivatives thereof or of mixtures of optionally substituted MDA and derivatives thereof with a higher homologous product, which comprises contacting, preferably washing, said catalyst with an aromatic compound, in at least partially liquid phase wherein the aromatic compound comprises a substituent having activating characteristics with respect to electrophilic substitution as compared to the aromatic compound without the said substituent.

The term "at least partially exhausted" in relation to the catalyst to be regenerated denotes a reduction in the activity and/or selectivity of the catalyst which has been used in a process as compared to the activity and/or selectivity of the catalyst prior to its use in the process.

By "corresponding aminal intermediate" is meant the amine-containing compound which is capable of undergoing a rearrangement reaction to produce the desired product, optionally substituted MDI and derivatives thereof.

Suitably, the optionally substituted MDI and derivatives thereof and, if present, a higher homologous product are produced by a process comprising the re-arrangement reaction of the corresponding aminal intermediate or the condensation reaction, preferably direct condensation reaction, between formaldehyde and optionally substituted aniline or a derivative thereof.

Preferably the condensation or rearrangement reaction is carried out at elevated temperature.

Preferably the catalyst is contacted with the aromatic compound at a temperature higher than that of the condensation and/or re-arrangement reaction in which the optionally substituted MDI and derivatives thereof is produced.

Preferably the catalyst is contacted, especially washed with the aromatic compound in equicurrent or concurrent or countercurrent flow with respect to the flow of the process reactants used to make the product.

In a preferred embodiment of the invention, there is provided a process for the regeneration of a zeolitic catalyst which is at least partially exhausted by use in the synthesis of optionally substituted methylenedianiline (MDA) and derivatives thereof or of mixtures of optionally substituted MDA and derivatives thereof with a higher homologous product by a process comprising the re-arrangement reaction of the corresponding aminal intermediate or the condensation reaction between formaldehyde and optionally substituted aniline or a derivative thereof, which regeneration process comprises contacting, preferably washing, said catalyst with an aromatic compound, in at least partially liquid phase and at a temperature higher than that of the condensation and/or re-arrangement reaction in which the optionally substituted MDI and derivatives thereof is produced wherein the aromatic compound comprises a substituent having activating characteristics with respect to electrophilic substitution as compared to the aromatic compound without the said substituent.

Suitably, the regeneration process may be repeated to successively regenerate the catalyst as desired.

The invention further provides a process for producing optionally substituted methylenedianiline (MDA) and derivatives thereof or of mixtures of optionally substituted MDA and derivatives thereof with a higher homologous product by a process comprising:

A) contacting a feedstock comprising i) the corresponding aminal intermediate or ii) formaldehyde and optionally substituted aniline or a derivative thereof with a zeolitic catalyst at elevated temperature to effect, in the case of feedstock i), a rearrangement reaction and, in the case of feedstock ii) a condensation reaction, to produce optionally substituted methylenedianiline (MDA) or a derivative thereof;

B) regenerating the at least partially exhausted catalyst by a process comprising contacting said catalyst with an aromatic compound, in at least partially liquid phase wherein the aromatic compound comprises a substituent having activating characteristics with respect to electrophilic substitution as compared to the aromatic compound without the said substituent at a temperature higher than that of step A); and optionally C) alternately further carrying out step A) and step B).

Preferably, the process described immediately above comprises a series of process steps of producing the desired product as described in step A), regenerating the catalyst as described in step B) and optionally repeating those steps in succession.

The aromatic compound for use in the present process for regenerating the catalyst comprises at least one substituent of the ring having an activating effect with respect to electrophilic substitution which is strong or intermediate as compared to the compound without the said substituent. Suitable substituents having a strong activating effect include amines, for example $-NH_2$, $-NHR$, and $-NR_2$, wherein R is as defined in formula I and $-OH$, and $-O^-$. Suitable substituents having an intermediate activating effect include for example, $-OR$, $-NHCOR_2$ substituents wherein $R_1$ and $R_2$ represent a $C_1-C_4$ (iso) alkyl, $C_4-C_{10}$ cycloalkyl, aromatic, alkylammatic or $C_6-C_{10}$ arylalkyl radical. Other substituents which provide an activating effect with respect to electrophilic substitution may also be employed as desired.

Preferred aromatic compounds according to the present invention are phenol and aromatic amines, especially aniline.

Any solid acid catalyst suitable for use in a re-arrangement and/or condensation reaction to produce optionally substituted MDA and derivatives thereof, and/or optionally substituted MDA and derivatives thereof mixed with a higher homologous product, may be subjected to the present regeneration process.

Catalysts particularly suitable for regeneration in the present process include zeolites having a "spaciousness index" from 2.5 to 19, silico-aluminas amorphous to X-rays, with a molar ratio $SiO_2/Al_2O_3$ from 10/1 to 500/1 and having a surface area from 500 to 1000 $m^2/g$, a porosity from 0.3 to 0.6 ml/g and a pore diameter from 2 to 50 nm, described in the above-mentioned Italian patent applications, together with the description of the synthesis of optionally substituted MDA, or optionally substituted MDA, mixed with a homologous higher product.

These catalysts may be used in any suitable form including, in the form of compressed powders, or extruded bodies (spheres, pellets or tablets) suitably after blending with an extrusion ligand.

The "spaciousness index" is a parameter which provides the real measurement of the pore amplitude of porous materials such as zeolites, of which a detailed description can be found in literature, for example in "Zeolites and Related Microporous Material: State of the Art 1994", Studies in Surface Science and Catalysis, vol. 84, 37, 1994, Elsevier Science B.V.

Preferably the at least partially exhausted catalyst is contacted, especially washed with the aromatic compound at a higher temperature than that of the re-arrangement and/or condensation reaction by which the optionally substituted MDI and derivatives thereof or optionally substituted MDA and derivatives thereof mixed with a homologous higher product are preferably produced.

As the rearrangement or condensation reaction is suitably carried out at a temperature from 50 to 200° C., the regeneration process is preferably effected at a temperature from 100 to 400° C., more preferably from 200 to 320° C. The pressure of the container where the regeneration is carried out is such as to maintain the aromatic compound in liquid or partially liquid phase.

Some illustrative but non-limiting examples are provided for a better understanding of the present invention and for its embodiment.

EXAMPLE 1

Synthesis of Aminal (Reaction Intermediate)

The reaction intermediate having the general formula:

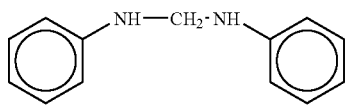

is prepared by condensation between aniline and formaldehyde. In particular, an aqueous solution at 37% of formaldehyde is charged, under stirring, into a reaction container containing aniline, so that the molar ratio of formaldehyde to aniline is four. The temperature is slowly increased to 50° C.

At the end of the addition the mixture is stirred for an hour and the organic phase consisting of aminal and non-reacted aniline is then separated in a separator funnel. The organic phase is then dried to a maximum water content of 1.25% and conserved for subsequent use.

EXAMPLE 2

Aminal at 30%—Regeneration with Aniline 10 cm$^3$ of beta zeolite extruded with a quantity of ligand ($Al_2O_3$) equal to 50% by weight, sieved to 70–100 mesh, was charged into a tubular reactor having a diameter of 12.5 mm and a length of 390 mm. A mixture of aminal (prepared according to Example 1) at 30% by volume in aniline was then fed to the reactor, at a temperature of 180° C., a pressure of 4 bars and an LHSV of 7.2 h$^{-1}$.

A total conversion of the-aminal feed is obtained, with a concentration of methylenedianiline (4,4' MDA+2,4' MDA) in the reaction product of 90%, the complement to 100% being trimers and tetramers of MDA. The test was carried out until the concentration of MDA in the reaction mixture dropped to below 84%. At this point the regeneration procedure of the partially exhausted catalyst was carried out.

The feeding of aminal was interrupted, and pure aniline was fed at the same space velocity. The catalytic bed was heated to a temperature of 230° C. creating a counter-pressure in the reactor of six bars and the temperature reached was maintained for 12 hours.

The catalytic bed was then brought back to the reaction temperature (180° C.) and, at the end of the reaction procedure described, the feeding of aminal was re-started, obtaining a total conversion of the aminal with a concentration of methylenedianiline (4,4' MDA+2,4' MDA) in the reaction product of 90.5%, the complement to 100% being trimers and tetramers of MDA.

The test was prolonged until the concentration of MDA in the reaction mixture dropped to below 81%. At this point a regeneration procedure of the partially exhausted catalyst, as described above, was carried out.

At the end of this second regeneration, the feeding of aminal was re-started, obtaining a total conversion of the aminal with a concentration of methylenedianiline (4,4' MDA+2,4' MDA) in the reaction product of 90.1%, the complement to 100% being trimers and tetramers of MDA.

The test was carried out until the concentration of MDA in the reaction mixture dropped to 37%; in this case the conversion of aminal was no longer total but decreased to 71%. At this point a regeneration procedure of the partially exhausted catalyst as described above, was carried out.

At the end of this third regeneration, the feeding of aminal was re-started, obtaining a total conversion of the aminal with a concentration of methylenedianiline (4,4' MDA+2,4' MDA) in the reaction product of 90.25%, the complement to 100% being trimers and tetramers of MDA.

EXAMPLE 3

Aminal at 70%—Regeneration with Aniline 10 cm$^3$ of beta zeolite extruded with a quantity of ligand ($Al_2O_3$) equal to 50% by weight, sieved to 70–100 mesh, was charged into a tubular reactor having a diameter of 12.5 mm and a length of 390 mm. A mixture of aminal (prepared according to Example 1) at 70% by volume in aniline was then fed to the reactor, at a temperature of 180° C., a pressure of 4 bars and an LHSV of 7.2 h$^{-1}$.

A total conversion of the aminal feed was obtained, with a concentration of methylenedianiline (4,4' MDA+2,4' MDA) in the reaction product of 72%, the complement to 100% being trimers and tetramers of MDA.

The test was continued until the concentration of MDA in the reaction mixture dropped to 47%, in this case there being no longer total conversion of the aminal which decreased to 94%. At this point the regeneration procedure of the partially exhausted catalyst was activated. The feeding of aminal was interrupted, and pure aniline fed at the same space velocity. The catalytic bed was heated to a temperature of 250° C. creating a counter-pressure in the reactor of six bars and the temperature reached was maintained for 12 hours.

The catalytic bed was then brought back to the reaction temperature (180° C.).

At the end of the reaction procedure described, the feeding of aminal was re-started, obtaining a total conversion of the aminal with a concentration of methylenedianiline (4,4' MDA+2,4' MDA) in the reaction product of 72.7%, the complement to 100% being trimers and tetramers of MDA.

EXAMPLE 4

Pure Aminal—Regeneration with Aniline)

10 cm$^3$ of beta zeolite extruded with a quantity of ligand ($Al_2O_3$) equal to 50% by weight, sieved to 70–100 mesh, was charged into a tubular reactor having a diameter of 12.5 mm and a length of 390 mm. Pure aminal (prepared according to Example 1) was then fed to the reactor, at a temperature of 180° C., a pressure of 4 bars and an LHSV of 7.2 h$^{-1}$.

A total conversion of the aminal feed was obtained, with a concentration of methylenedianiline (4,4' MDA+2,4' MDA) in the reaction product of 66%, the complement to 100% being trimers and tetramers of MDA. The test was continued until the concentration of MDA in the reaction mixture dropped to below 43%. At this point the regeneration procedure of the partially exhausted catalyst was activated.

The feeding of aminal was interrupted, pure aniline was fed at the same space velocity and the catalytic bed was heated to a temperature of 250° C. creating a counter-pressure in the reactor of six bars.

The temperature reached was maintained for 12 hours, and the catalytic bed was then brought back to the reaction temperature (180° C.).

At the end of the reaction procedure described, the feeding of pure aminal was re-started, obtaining a total conversion of the aminal with a concentration of methylenedianiline (4,4' MDA+2,4' MDA) in the reaction product of 66.5%, the complement to 100% being trimers and tetramers of MDA.

EXAMPLE 5

Comparative 10 cm³ of beta zeolite extruded with a quantity of ligand (Al₂O₃) equal to 50% by weight, sieved to 70–100 mesh, was charged into a tubular reactor having a diameter of 12.5 mm and a length of 390 mm. A mixture of aminal (prepared according to the Example 1) at 30% by volume in aniline was then fed to the reactor, at a temperature of 180° C., a pressure of 4 bars and an LHSV of 7.2 h⁻¹.

A total conversion of the aminal feed was obtained, with a concentration of methylenedianiline (4,4' MDA+2,4' MDA) in the reaction product of 66.5%, the complement to 100% being trimers and tetramers of MDA. The test was continued until the concentration of MDA in the reaction mixture dropped to below 42%. At this point the regeneration procedure of the partially exhausted catalyst was carried out.

The feeding of aminal was interrupted and mesitylene (1,3,5-trimethylbenzene) was fed at the same space velocity. The catalytic bed was heated to a temperature of 250° C. creating a counter-pressure in the reactor of eight bars.

The temperature reached was maintained for 12 hours, and the catalytic bed was then brought back to the reaction temperature (180° C.).

At the end of the reaction procedure described, the feeding of aminal was re-started, obtaining a total conversion of the aminal with a concentration of methylenedianiline (4,4' MDA+2,4' MDA) in the reaction product of 37%, the complement to 100% being trimers and tetramers of MDA. The selectivity of the
catalyst as regenerated was not as high as the initial selectivity level of the catalyst.

EXAMPLE 6

Comparative 10 cm³ of beta zeolite extruded with a quantity of ligand (Al₂O₃) equal to 50% by weight, sieved to 70–100 mesh, was charged into a tubular reactor having a diameter of 12.5 mm and a length of 390 mm. A mixture of aminal (prepared according to Example 1) at 30% by volume in aniline was then fed to the reactor, at a temperature of 180° C., a pressure of 4 bars and an LHSV of 7.2 h⁻¹.

A total conversion of the aminal feed was obtained, with a concentration of methylenedianiline (4,4' MDA+2,4' MDA) in the reaction product of 90%, the complement to 100% being trimers and tetramers of MDA. The test was continued until the concentration of MDA in the reaction mixture dropped to below 84%. At this point the regeneration procedure of the partially exhausted catalyst was carried out.

The feeding of aminal was interrupted, n-decane was fed at the same space velocity and the catalytic bed was heated to a temperature of 230° C.

The temperature reached was maintained for 12 hours, and the catalytic bed was then brought back to the reaction temperature (180° C.).

At the end of the reaction procedure, the feeding of aminal at 30% was re-started, obtaining a total conversion of the aminal with a concentration of methylenedianiline (4,4' MDA+2,4' MDA) in the reaction product of 72%, the complement to 100% being trimers and tetramers of MDA.

The test was continued for the same period of time as the test described in Example 2 and in this case the concentration of MDA in the reaction product dropped to 43% whereas there was not total conversion of aminal this being at 69%.

The regeneration was repeated with n-decane as described above and at the end of the reaction process described, the feeding of aminal at 30% was re-started, providing a total conversion of the aminal with a concentration of methylenedianiline (4,4' MDA+2,4' MDA) in the reaction product of 39%. The aminal conversion was no longer total but was 63%.

The test was carried out for the same period as the test described in Example 2, in this case the concentration of MDA in the reaction product dropped to 21% whereas the aminal conversion was no longer total but was at 42%.

What is claimed is:

1. A process for the regeneration of a zeolitic catalyst which is at least partially exhausted by use in the synthesis of optionally sudstituted methylenedianiline (MDA) and derivatives thereof or of a mixture of optionally substituted MDA and derivatives thereof with a higher homologous product, which comprises contacting said catalyst with an aromatic compound, in at least partially liquid phase wherein the aromatic compound comprises at least one substituent having activating characteristics with respect to electrophilic substitution as compared to the aromatic compound without the said substituent wherein the substituent having activating characteristics is selected from $NH_2$, $-NHR$, $-NR_2$, $-OH$, $-O^-$, $-OR^1$, or $-NHCOR^2$ substituents wherein R is hydrogen, a $C_1-C_8$ alkyl, $C_4-C_{10}$ cycloalkyl $C_6-C_{12}$ aromatic radical. $R^1$ and $R^2$ represent a $C_1-C_4$ (iso)alkyl, $C_4-C_{10}$ cycloalkyl, aromatic, alkylaromatic or $C_6-C_{10}$ arylakyl radical.

2. A process according to claim 1 in which the optionally substituted methylenedianiline (MDA) and derivatives thereof or the mixture of optionally substituted MDA and derivatives thereof with a higher homologous product comprise a compound of formula (I):

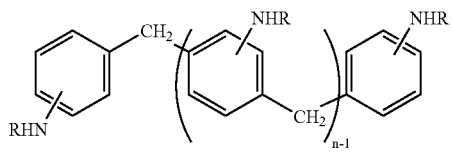

wherein R represents independently hydrogen, a $C_1-C_8$ alkyl, $C_4-C_{10}$ cycloalkyl $C_6-C_{12}$ aromatic radical and n is an integer greater than or equal to one, such as to give a functionality ranging from 2 to 6.

3. A process according to any one of claims 1 and 2 wherein the at least one substituent of the aromatic ring has a strong activating effect and is selected from $-NH_2$, $-NHR$, $-NR_2$, $-OH$ or $-O^-$ groups.

4. A process according to any one of claims 1 and 2 wherein the at least one substituent of the aromatic ring has an intermediate activating effect and is selected from $-OR^1$, or $-NHCOR^2$ groups wherein $R^1$ and $R^2$ represent a $C_1-C_4$ (iso) alkyl, $C_4-C_{10}$ cycloalkyl, aromatic, alkylaromatic or $C_6-C_{10}$ arylalkyl radical.

5. A process according to claim 1 wherein the aromatic compound is selected from phenol and aniline.

6. A process according to claim 1 wherein the catalyst is selected from zeolites with a "spaciousness" index ranging from 2.5 to 19, or silico-aluminas amorphous to X-rays, with a molar ratio $SiO_2/Al_2O_3$ from 10/1 to 500/1 and having a surface area from 500 to 1000 m²/g, a porosity from 0.3 to 0.6 ml/g and a pore diameter from 2 to 50 nm.

7. A process according to claim 1 in which the optionally substituted MDA and derivatives thereof and, if present, a higher homologous product are produced by a process comprising the re-arrangement reaction of the corresponding aminal intermediate of the condensation reaction between formaldehyde and optionally substituted aniline or a derivative thereof at elevated temperature.

8. A process according to claim 7 in which the catalyst is contacted with the aromatic compound at a temperature higher than that of the condensation and/or re-arrangement reaction in which the optionally substituted MDA and derivatives thereof is produced.

9. A process according to any one of claims 7 and 8 in which the catalyst is contacted, with the aromatic compound in equicurrent or concurrent or countercurrent flow with respect to the flow of the process reactants used to make the product.

10. A process according to claim 1 wherein the contacting of the catalyst with the aromatic compound takes place at a temperature ranging from 100 to 400° C.

11. A process for the regeneration of a zeolitic catalyst which is at least partially exhausted by use in the synthesis of optionally substituted methylenedianiline (MDA) and derivatives thereof or of mixtures of optionally substituted MDA and derivatives thereof with a higher homologous product by a process comprising the re-arrangement reaction of the corresponding aminal intermediate of the condensation reaction between formaldehyde and optionally substituted aniline or a derivative thereof, which regeneration process comprises contacting, said catalyst with an aromatic compound, in at least partially liquid phase and at a temperature higher than that of the condensation and/or re-arrangement reaction in which the optionally substituted MDA and derivatives thereof is produced wherein the aromatic compound comprises a substituent having activating characteristics with respect to electrophilic substitution as compared to the aromatic compound without the said substituent wherein the substituent having activating characteristics is selected from $NH_2$, —NHR, —$NR_2$, —OH, —O⁻, —$OR^1$, or —$NHCOR^2$ substituents wherein R is hydrogen, a $C_1$–$C_8$ alkyl, $C_4$–$C_{10}$ cycloalkyl $C_6$–$C_{12}$ aromatic radical, $R^1$ and $R^2$ represent a $C_1$–$C_4$ (iso)alkyl, $C_4$–$C_{10}$ cycloalkyl, aromatic, alkylaromatic or $C_6$–$C_{10}$ arylakyl radical.

* * * * *